United States Patent [19]

Lazar

[11] Patent Number: 5,393,921
[45] Date of Patent: Feb. 28, 1995

[54] PROCESS FOR SYNTHESIZING O-SUBSTITUTED OXIME COMPOUNDS AND CONVERSION TO THE CORRESPONDING O-SUBSTITUTED HYDROXYLAMINE

[75] Inventor: Harvey A. Lazar, Silver Spring, Md.

[73] Assignee: The Gillette Company, Boston, Mass.

[21] Appl. No.: 86,859

[22] Filed: Jul. 7, 1993

[51] Int. Cl.$^6$ ............................................. C07C 53/00
[52] U.S. Cl. ..................................... 562/512; 558/2; 558/3; 558/7; 562/405; 562/430; 562/440; 562/507; 562/556; 562/560; 564/256; 564/301
[58] Field of Search ............... 562/512, 560, 405, 430, 562/440, 507, 556; 564/301, 256; 558/2, 3, 7

[56] References Cited

U.S. PATENT DOCUMENTS

| | | | |
|---|---|---|---|
| 2,470,083 | 5/1949 | Hartung | 562/560 |
| 3,104,258 | 9/1963 | Ferris . | |
| 3,207,787 | 9/1965 | Levy | 564/301 |
| 3,247,243 | 4/1966 | Villani | 564/301 |
| 3,839,449 | 10/1974 | Herold . | |
| 4,038,317 | 7/1977 | Wermuth et al. . | |
| 4,052,194 | 10/1977 | Wilcox | 562/560 |
| 4,425,360 | 1/1984 | Wolff | 562/560 |
| 4,584,014 | 4/1986 | Patterson | 562/560 |
| 4,739,118 | 4/1988 | Elbe . | |
| 4,948,916 | 8/1990 | Uohama et al. . | |
| 4,959,495 | 9/1990 | Curran | 562/560 |
| 4,973,753 | 11/1990 | Lantzsch et al. . | |
| 4,981,996 | 1/1991 | Wyss et al. | 564/300 |
| 5,075,504 | 12/1991 | Schneider | 564/301 |
| 5,095,149 | 3/1992 | Tani | 562/560 |

FOREIGN PATENT DOCUMENTS

| | | | |
|---|---|---|---|
| 1110642 | 10/1981 | Canada . | |
| 1259629 | 9/1989 | Canada . | |
| 0023560 | 2/1981 | European Pat. Off. . | |
| 0158159 | 10/1985 | European Pat. Off. . | |
| 259850 | 3/1988 | European Pat. Off. | 564/301 |
| 0121701 | 8/1988 | European Pat. Off. . | |
| 62-215557 | 9/1987 | Japan | 562/560 |
| 347330 | of 1972 | U.S.S.R. . | |
| WO89/11473 | 11/1989 | WIPO . | |

OTHER PUBLICATIONS

Ault, "Techniques and Experiments for Organic Chemistry", 4th Ed., pp. 302–307 (1983).
"The Preparation of Aminoxyacetic Acid", Chemical World, vol. 9, No. 30, pp. 397–399, 1989. Dept. of Chemistry, Lanzhou University (Translation only).
"Carboxymethoxylamine Hemihydrochloride", Organic Syntheses Collective, vol. 3.
Dunstan and Goulding: "The Action of Alkyl"; J. Chem. Soc., 23, 628, 1901.
"Carboxymethoxylamine", J. Am. Chem. Soc., vol. LVIII, 58 2020 (1936).

Primary Examiner—Michael L. Shippen
Attorney, Agent, or Firm—Burns, Doane, Swecker & Mathis

[57] ABSTRACT

A process for synthesizing O-substituted oxime compounds, which includes (a) reacting an alkali metal or alkaline earth metal hydroxide compound and a solution of an oxime compound to form a first mixture including the alkali metal or alkaline earth metal salt of the oxime compound and water; and (b) adding an organohalide compound while stirring to the first mixture to form a second mixture including an O-substituted oxime compound, the alkali metal or alkaline earth metal salt of the oxime compound, water, unreacted organohalide compound and excess oxime compound. The second mixture is heated in the presence of an amount of water sufficient to react hydroxide with the unreacted organohalide compound to obtain an O-substituted oxime compound substantially free of unreacted organohalide compound.

In a further embodiment, the O-substituted oxime compound can be hydrolyzed to the corresponding O-substituted hydroxylamine. The process is especially useful in the conversion of O-substituted oxime compounds to the corresponding aminooxy-compound.

14 Claims, No Drawings

PROCESS FOR SYNTHESIZING O-SUBSTITUTED OXIME COMPOUNDS AND CONVERSION TO THE CORRESPONDING O-SUBSTITUTED HYDROXYLAMINE

BACKGROUND OF THE INVENTION

The present invention relates to a process for synthesizing O-substituted oxime compounds. In particular, the present invention relates to the synthesizing of O-substituted oxime compounds, which process is especially useful in the conversion thereof to the corresponding O-substituted hydroxylamine.

Typically, O-alkyl oximes have been produced by reacting an oxime with an organohalide, such as methyl bromide or methyl iodide, and an alkali metal alkoxide, such as sodium methoxide. For example, Dunstan and Goulding in J. Chem. Soc., 23, 628, 1901 disclose the O-methylation of acetone oxime by reacting acetone oxime with methyl iodide and sodium methoxide.

EPO Patent Application No. 23,560 to Linhart et al. discloses two procedures for producing O-alkyl oximes. The first procedure relates to a modification of the conventional method according to a two step process. In the first step of the procedure, an oxime is converted to the salt form by reaction with an alkali metal alkoxide. The oxime salt is isolated and dried. In the second step of the procedure, the alkali metal salt of the oxime is reacted with an alkyl bromide or alkyl chloride in an aprotic-dipolar solvent. Specifically, Linhart et al. discloses the conversion of the oxime to the corresponding sodium salt by reaction with sodium methoxide, isolating and drying the salt, and then reacting the salt with methyl chloride as the alkylating agent to produce the O-alkyl oxime.

The second procedure disclosed by Linhart et al. relates to the O-alkylation of oximes by reacting oximes with powdered sodium hydroxide and an organohalide in the presence of water by using an aprotic-dipolar solvent. The O-substituted oxime products are purified by fractional distillation.

H. S. Anker and H. T. Clarke, "Carboxymethoxylamine Hemihydrochloride", Org. Synth, Col. Vol. III, p. 173 discloses a process for the preparation of hydroxylamine O-acetic acid by reacting α-bromoacetic acid and acetoxime in the presence of sodium hydroxide in an aqueous reaction medium and hydrolyzing the resulting acetoxime O-acetic acid. Bromoacetic acid is used in excess in the process. However, Borek and Clarke, "Carboxymethoxylamine", J. Am. Chem. Soc., 58 2020 (1936) is cited therein for the use of chloroacetic acid in a reaction with acetoxime in which poorer yields (46-49%) of a product which was difficult to purify was recorded. The reaction requires heating in a tube at approximately 100° C. The aqueous solution is saturated with solid sodium chloride prior to exhaustive extractions with ethyl ether to yield crude acetoxime O-acetic acid.

EPO Patent Application No. 158,159 to Mathew et al. relates to a process for producing O-substituted oxime compounds, specifically O-alkyl substituted oximes, by reacting an alkali metal or alkaline earth metal hydroxide compound with an excess of oxime reactant to form the oxime salt, removing water from the system by azeotropic distillation, and thereafter reacting the oxime salt with an organohalide compound under substantially anhydrous conditions. A key feature in this process is the azeotropic distillation of the oxime salt to remove all or a portion of the water from the reaction mixture prior to reacting the salt with an organohalide compound under substantially anhydrous conditions.

PCT/US89/02188 to Chempolil T. Mathew, relates to a process for producing O-substituted oximes under anhydrous conditions by reacting an alkali metal or alkaline earth metal hydroxide compound in an organic solvent with an excess of oxime reactant to form the oxime salt, removing water from the system by azeotropic distillation, and thereafter reacting at least about a two molar excess of the oxime salt in situ with an alpha-halocarboxylic acid and isolating the resultant O-substituted oxime compound from the reaction mixture. A key feature in this process is the azeotropic distillation of the oxime salt to remove all or a portion of the water from the reaction mixture prior to reacting at least about a two molar excess of the oxime salt in situ with an alpha-halocarboxylic acid. The O-substituted oxime compound can be isolated from the reaction mixture and purified employing conventional techniques.

Zhang, Feng and Shi, "The Preparation of Aminoxyacetic Acid", Chem. World, Vol. 9, No. 30, pp. 397–399, 1989 discloses condensing acetone oxime and chloroacetic acid in the presence of a solid acid or halide of a quaternary ammonium salt catalyst, organic solvent and sodium hydroxide at room temperature to form acetone oxime-acetic acid. Chloroacetic acid is added in excess relative to the acetone oxime. Benzene is used as the organic solvent. An approximately 6% aqueous solution of sodium hydroxide is used in an amount equimolar to the combined amount of acetone oxime and chloroacetic acid. After completion of the reaction, the aqueous solution is saturated with sodium chloride prior to exhaustive extractions with ethyl ether. Acetone oxime-acetic acid is obtained as a crude yellow oil which requires purification by vacuum distillation prior to hydrolysis to aminooxyacetic acid hemihydrochloride.

It is therefore an object of the present invention to provide an O-substituted oxime compound without the need for isolation or purification of an intermediate oxime salt compound.

Another object of the present invention is to provide a process for synthesizing an O-substituted oxime compound without removing, by azeotropic distillation or any means, all or a portion of the water added to the reaction mixture or formed during the production of an intermediate oxime salt compound.

A further object of the present invention is to provide a process for synthesizing an O-substituted oxime compound wherein the reaction of an intermediate oxime salt compound with an organohalide is not performed under substantially anhydrous conditions.

Another object of the present invention is to provide a process for synthesizing an O-substituted oxime compound having improved economics by avoiding the use of expensive alkoxides and by using organochlorides in place of bromides and iodides.

A further object of the present invention is to provide a process for synthesizing an O-substituted oxime compound which does not require an inert atmosphere.

Another object of the present invention is to provide an efficient process for synthesizing an O-substituted oxime compound in high yield and purity.

A further object of the present invention is to provide an efficient process for synthesizing aminooxyacetic acid in high yield and purity.

Another object of the present invention is to provide a process for synthesizing an O-substituted oxime compound wherein the O-substituted oxime compound can be extracted from the reaction medium at room temperature.

A further object of the present invention is to provide a process for synthesizing an O-substituted oxime compound without requiring the addition of a salt during the extraction of the O-substituted oxime compound.

Another object of the present invention is to provide a process for synthesizing an O-substituted oxime compound substantially free of a haloacetic acid.

A further object of the present invention is to provide a process for synthesizing an O-substituted oxime compound in the presence of an amount of water and under reaction conditions sufficient to remove substantially all of the haloacetic acid.

SUMMARY OF THE INVENTION

In accordance with an aspect of the present invention, these objects are achieved by a process which includes reacting an alkali metal or alkaline earth metal hydroxide compound and a solution of an oxime compound to form a first mixture including an alkali metal or alkaline earth metal salt of the oxime compound and water; and adding an organohalide compound while stirring to form a second mixture including an O-substituted oxime compound, the alkali metal or alkaline earth metal salt of the oxime compound, water, unreacted organohalide compound and excess oxime compound. The second mixture may be further heated in the presence of an amount of water sufficient to react hydroxide with the unreacted organohalide to obtain an O-substituted oxime compound substantially free of unreacted organohalide compound.

In accordance with a further aspect of the present invention, these objects are achieved by a process which additionally includes the hydrolysis of the O-substituted oxime compound to the corresponding O-substituted hydroxylamine.

In accordance with another aspect of the present invention, these objects are achieved by a process which includes not subjecting the reaction mixture of an alkali metal or alkaline earth metal salt of the oxime compound and water to azeotropic distillation, or any means, to remove all or a portion of the water from the mixture.

DETAILED DESCRIPTION OF THE PREFERRED EMBODIMENTS

The present invention is a process for synthesizing O-substituted oxime compounds. The process is especially useful in the conversion of O-substituted oxime compounds to the corresponding O-substituted hydroxylamine, such as an aminooxy-compound. The process includes reacting an alkali metal or alkaline earth metal hydroxide compound and a solution of an oxime compound to form a first mixture including the alkali metal or alkaline earth metal salt of the oxime compound and water. The process is performed without removing, by azeotropic distillation or any means, all or a portion of the water added to the reaction mixture or formed during the production of the intermediate oxime salt compound. Thereafter, an organohalide compound is added while stirring to form a second mixture including an O-substituted oxime compound, the alkali metal or alkaline earth metal salt of the oxime compound, unreacted organohalide compound, excess oxime compound and water. The second mixture is further heated in the presence of an amount of water sufficient to react hydroxide with the unreacted organohalide to obtain an O-substituted oxime compound substantially free of unreacted organohalide compound. In a further step, the O-substituted oxime compound can be hydrolyzed to the corresponding O-substituted hydroxylamine.

In a preferred embodiment of the process of the present invention, initially, a solution of an oxime compound is prepared. A solid oxime compound can be added to a suitable organic solvent to form the solution. The amount of solvent is not critical and can vary widely. Typically, the total amount of solvent can vary from about 100% to about 700% by weight based on the total weight of the oxime reactant. The preferred total amount of solvent is from about 500% to about 700% percent by weight of the oxime reactant. Alternatively, when the oxime compound is a liquid, no solvent is needed.

Oxime compounds which are useful as reactants in the process of the present invention include compounds having the functional group —C=N—OH and are well known to those of ordinary skill in the art. Suitable oxime compounds include compounds of the formula $R_1R_2C=NOH$ in which $R_1$ and $R_2$ are the same or different and are hydrogen, or substituted or unsubstituted arylthio, arylsulfonyl, arylsulfinyl, alkylsulfinyl, alkylsulfonyl, alkyl, alkynyl, cycloalkyl, alkenyl, alkoxy, alkoxyalkyl, alkylthio, aryl or aralkyl, or $R_1$ and $R_2$ together may form a substituted or unsubstituted alkylene or alkenylene chain completing a cycloalkyl or cycloalkenyl group containing from 3 to about 7 carbon atoms within the ring structure, wherein permissible substituents are one or more alkyl, alkoxy, alkylthio, amido, carboxy, fluoro, nitro, cyano, alkoxycarbonyl, perfluoroalkyl, arylthio, phenoxy, alkylsulfinyl, alkylsulfonyl, arylsulfinyl, alkylaminocarbonyl, dialkylaminocarbonyl, alkylthiocarbonyl, or arylsulfonyl groups.

The oxime compounds utilized as reactants in the process of the present invention can be conveniently prepared according to conventional methods. For example, these compounds can be conveniently prepared by reacting an appropriate aldehyde or ketone with hydroxylamine salts, optionally in the presence of an alkali metal hydroxide, an alkali metal carbonate or ammonia. Another method involves reacting the corresponding aldehyde or ketone in a water medium with sodium nitrite, sodium bisulfite and sulfur dioxide. Preferred oximes for use in the practice of the present invention include, for example, acetone oxime, 2-butanone oxime, cyclohexanone oxime, and vanillin oxime. Most preferred is acetone oxime, which can be obtained commercially or prepared by reacting acetone with hydroxylamine under alkaline conditions.

As used herein, a "suitable organic solvent" is any organic solvent which does not react with the hydroxide and oxime reactants under the reaction conditions of the process, and which is capable of forming a solution of the oxime. Illustrative of suitable solvents are nonpolar solvents as for example aliphatic and cycloaliphatic hydrocarbons, such as hexane, cyclohexane, heptane, cyclopentane, pentane, isooctane, and the like; aromatic solvents such as benzene, toluene, xylene and the like; and halohydrocarbons such as carbon tetrachloride, methylene dichloride, chlorofluoromethane, dichlorodifluoromethane, trichlorotrifluoroethane, chloroform, and the like. Preferred non-polar organic solvents for use in the practice of this invention are fluorohydrocarbon solvents, hydrocarbon solvents and aromatic solvents, and particularly preferred for use in the process are aromatic solvents such as toluene and xylene, and hydrocarbon solvents such as pentane, isooctane, cyclohexane and the like. Other hydrocarbon solvents, both aromatic and non-aromatic, also would be suitable.

In accordance with the process of the present invention an aqueous solution of an alkali metal or alkaline earth metal hydroxide compound is added, with stirring, to the oxime solution to form a first mixture of an alkali metal or alkaline earth metal salt of the oxime compound and water. The oxime salt is in the form of a thick slurry, which is further stirred. The mole equivalent ratio of hydroxide/oxime is preferably from about 0.5/1 to about 5/1, most preferably from about 1/1 to about 1.5/1. The concentration of hydroxide is preferably from about 10% to about 50%, most preferably from about 40% to about 50%.

Any alkali metal or alkaline earth metal hydroxide compound is suitable for use in the process of the present invention such as lithium hydroxide, potassium hydroxide, calcium hydroxide, magnesium hydroxide, sodium hydroxide, and the like. Alkali metal hydroxide compounds are preferred for use in the practice of the present invention. Particularly preferred for use are potassium hydroxide and sodium hydroxide, and most preferred is sodium hydroxide. The form of the alkali metal or alkaline earth metal hydroxide is not critical. The hydroxide can be added in solution form or can be added as a solid, in which case the required amount of water to make the desired concentration is added beforehand.

The alkali metal or alkaline earth metal salt of the oxime compound is reacted in situ with an appropriate organohalide compound with stirring to produce the corresponding O-substituted oxime compound, according to the process of the present invention. The organohalide compound is the limiting reagent and is added to the mixture of the alkali metal or alkaline earth metal salt of the oxime compound and water to form a second mixture including the O-substituted oxime compound, excess unreacted oxime compound, unreacted organohalide compound, the alkali metal or alkaline earth metal salt of the oxime compound and water. This step is performed without removing, by for example azeotropic distillation, all or a portion of the water added to the reaction mixture or formed during the production of the oxime salt compound. The organohalide Can be added dropwise as a liquid, dropwise as a solution dissolved in an organic solvent, or portion-wise as a solid.

An excess amount of the oxime compound is used relative to the organohalide. The mole equivalent ratio of the oxime/organohalide is preferably from about 1.5/1 to about 6/1, most preferably from about 2.5/1 to about 3/1.

Organohalide compounds utilized as reactants in the process of the present invention as well as methods for their preparation are well known in the art. For example, such compounds can be readily prepared by reacting a halogen, as for example chlorine, with an appropriate organo compound. While any organohalide compound can be used in the process of the present invention, organochloride compounds are preferred for the economic reasons of greater availability and lower cost.

Suitable organohalide compounds have an organic moiety having a primary, secondary or tertiary carbon atom bonded to the halogen of the organohalide wherein the carbon atoms of the organic moiety may be optionally substituted with one or more substituents that are inert during the process.

Preferred organohalide compounds are halogenated carboxylic acids of the formula:

XCH(R)COOH 

wherein R is a hydrogen, a phenyl group, or a $C_1$-$C_{14}$ alkyl group which is unsubstituted or substituted by a phenyl group, a hydroxy group, a carboxy group, a benzyloxy or benzyloxycarbonyl group, a halogen or an amino group and wherein X is a halogen, preferably I, Cl or Br, most preferably Cl.

Particularly preferred is chloroacetic acid or bromoacetic acid for use in preparing acetone oxime-O-acetic acid. For preparing acetone oxime derivatives of other carboxylic acids, e.g., acetone oxime-O-octanoic acid or acetone oxime-O-hexadecanoic acid, the appropriate halocarboxylic acid would also be preferred.

The reaction temperature of the process of the present invention can vary from about 5° C. to about 60° C., with a range of from about 20° C. to about 55° C. being preferred. The reaction is exothermic and the temperature can rise to over 60° C. unless the rate of addition of the hydroxide and organohalide is controlled or external cooling is applied. In a preferred embodiment, the temperature is controlled by controlling the rate of addition of the hydroxide and the organohalide. Alternatively, for room temperature reactions, for example, the reaction flask can be kept in a circulating tapwater bath. Further, the reaction zone can be fitted with one or more internal and external heat exchangers in order to control temperature fluctuations, or to prevent any possible "runaway" reaction temperatures.

According to an embodiment of the process of the present invention, water is added and the second mixture is further heated to about 50° C. for about one hour to facilitate the reaction of hydroxide with the unreacted organohalide compound. Some variation in the amount of water added is acceptable, provided there is an amount sufficient to facilitate consumption of the unreacted organohalide compound. This additional water also facilitates subsequent pH adjustment during isolation of the product. However, too little water makes pH adjustment more difficult and too much water reduces the efficiency of the extractions, particularly at pH 1.

The O-substituted oxime compound can be isolated from the reaction mixture according to conventional techniques. For example, after heating the pH of the aqueous phase is adjusted to about 10 with thorough mixing. The organic layer is separated and the aqueous layer is washed with organic solvent to remove the excess unreacted oxime compound. The excess unreacted oxime compound can be recovered from the organic solvent by extracting into a highly alkaline aqueous solution.

The aqueous phase is acidified to about pH 1 and extracted with organic solvent. The addition of an appropriate amount of water, as discussed above, prevents the need for adding salt in order to quantitatively extract the O-substituted oxime compound into the organic solvent. At pH 1, any hydrolysis to the corresponding O-substituted hydroxylamine can be substantially reduced by doing the extractions quickly. The extract can be concentrated under reduced pressure to provide the desired O-substituted oxime compound. By following the procedure of the present invention, there is no need to keep the solvents cold during the extraction.

Preferably, the O-substituted oxime compound product is isolated from the reaction medium by extraction with a suitable solvent and the extract concentrated under reduced pressure. The O-substituted oxime compound product can also be isolated from the reaction mixture and purified employing other techniques such as evaporation, distillation, recrystallization, and the like.

The process of the present invention is carried out over a period of time sufficient to produce the desired compound in adequate yield. Reaction times are influenced to a significant degree by the reactants, the reaction temperature, the concentration and choice of reactants, the choice and concentration of reaction solvent and by other factors known to those skilled in the art. In general, reaction times can vary from about an hour to about 24 hours or longer. However, increasing the reaction time to 24 hours or more does not appear to increase yield.

The O-substituted oximes produced by the process of the present invention are valuable as intermediates in the production of O-substituted hydroxylamines, as for example, aminooxyacetic acid. Accordingly, in a further embodiment of the process of the present invention, the O-substituted oxime compound is hydrolyzed to the corresponding O-substituted hydroxylamine. Specifically, O-substituted hydroxylamines may be produced by hydrolysis, preferably acid hydrolysis using non-oxidizing acids such as hydrochloric acid, sulfuric acid, phosphoric acid, p-toluene sulfonic acid, and the like, of the O-substituted oximes produced by the present invention. The hydrolysis can be conducted for a period of time of between about one hour and about 24 hours. The temperature of the hydrolysis can be between about 25° C. and about 120° C., preferably about 40° C. to about 60° C. Optionally, the hydrolysis can be conducted under a vacuum. When conducted under a vacuum, a vacuum of from about 1 mm Hg to about 125 mm Hg is preferred, and a vacuum of from about 50 mm Hg to about 125 mm Hg is most preferred.

The hydrolysis may be conducted in the oxime solution without isolation of the O-substituted oxime. In a preferred embodiment, the product is purified, as noted above, in the presence of an amount of water sufficient to react hydroxide with the unreacted organohalide compound to produce an O-substituted oxime compound substantially free of unreacted organohalide compound. The O-substituted oxime is then hydrolyzed to the corresponding O-substituted hydroxylamine as noted above.

Alternatively, the hydrolysis may be conducted after isolation of the O-substituted oxime. For example, aminooxyacetic acid may be produced by hydrolysis of the corresponding acetone oxime-O-acetic acid which has been readily extracted into water, as noted above.

Particularly preferred is the hydrolysis of the corresponding O-substituted oxime compounds to the O-substituted hydroxylamine compounds of the formula:

$$H_2N-O-CH(R)COOH$$

wherein R is a hydrogen, a phenyl group, or a $C_1$-$C_{14}$ alkyl group which is unsubstituted or substituted by a phenyl group, a hydroxy group, a carboxy group, a benzyloxy or benzyloxycarbonyl group, a halogen or an amino group.

The O-substituted oxime compound produced by the process of the present invention is substantially free of organohalide impurities. Accordingly, the resultant O-substituted hydroxylamines are also substantially free of organohalide impurities. Thus, the products, as for example aminooxyacetic acid, are suitable for use in applications which require compounds substantially free of organohalide impurities, such as chloroacetic acid and the like.

The process of the present invention can be conducted in ambient atmosphere. While the process can be performed under an inert atmosphere, this is not required. Preferably, the process is not conducted under an inert atmosphere.

The process of the present invention is conducted in the absence of a catalyst.

The process of the present invention can be conducted in a batch, semicontinuous or continuous fashion. The reactants and reagents may be initially introduced into the reaction zone batchwise or they may be continuously or intermittently introduced in such a zone during the course of the process. Means to introduce and adjust the quantity of reactants, either intermittently or continuously into the reaction zone during the course of the reaction can be conveniently utilized in the process especially to maintain the desired molar ratio of the reaction solvent, reactants and reagents. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressures.

In the process of the present invention, mixing includes varying the degree of agitation of the reaction mixture. Mixing by vibration, shaking, stirring, rotation, oscillation, ultrasonic vibration, and the like are illustrative of the type of mixing contemplated. Such means are available and well known to those skilled in the art.

The following examples illustrate preferred embodiments of the process of the present invention. The examples are not intended to be construed as limitations upon the process of the present invention.

EXAMPLE 1

To a 3 liter 3-neck round bottom flask equipped with an overhead mechanical stirrer, an addition funnel with a pressure equalizing sidearm, and a thermometer were added at room temperature, with stirring, 132 grams (1.8 moles) of acetone oxime and 0.6 liters of xylene. After dissolution of the oxime, a 50% aqueous solution of sodium hydroxide (144 grams, 1.8 moles) was added over a period of 5 to 10 minutes, at a rate which prevented the temperature from rising above about 50° C. The resulting thick white slurry was stirred for an additional 15 minutes. A solution of 57 grams (0.6 moles) of chloroacetic acid in 450 milliliters of xylene was added dropwise through the addition funnel at a rate to keep the reaction temperature below about 55° C. During this time, the thick white slurry began to dissolve and become thinner. Vigorous stirring was continued for an additional 3 hours, by which time the initial white slurry had become a cloudy light yellow mixture and the temperature had fallen to below 30° C. The contents of the flask were transferred to a beaker and diluted with 165 milliliters of distilled water. The pH of the bottom aqueous phase was adjusted to about 10 with 10M HCl. After thorough mixing, the top organic layer was separated and the yellow aqueous layer was washed with 2×600 milliliters of xylene to remove the excess acetone oxime. The aqueous layer was acidified to about pH 1 with 10M HCl and quickly extracted with 4×600 milliliters of xylene. The xylene layers were combined and rotary evaporated under vacuum to produce 51.7 grams of acetone oxime-O-acetic acid as a white crystalline solid, m.p. 74°-76° C. The yield was 66%.

EXAMPLE 2

To a 2-liter 3-neck round bottom flask equipped with an overhead mechanical stirrer and a thermometer were added at room temperature, with stirring, 110 grams (1.5 moles) of acetone oxime and 840 milliliters of xylene. After dissolution of the oxime, 60 grams of distilled water were added followed by 60 grams (1.5 moles) of sodium hydroxide pellets over a period of about 15 minutes, which allowed the temperature to remain below 35° C. The resulting mixture was stirred for an additional 15 minutes. Fifty-seven grams (0.6 moles) of solid chloroacetic acid were added over a 15 minute period, which kept the reaction temperature below about 60° C. Vigorous stirring was continued for an additional 3 hours, by which time the temperature had fallen to below 30° C. At the end of 3 hours, 130 milliliters of distilled water were added and the mixture was stirred for an additional 1 hour at about 50° C. After being allowed to cool to room temperature, the pH of the bottom aqueous phase was adjusted to about 10 with 10M HCl. After thorough mixing, the top organic layer was separated and the yellow aqueous layer was washed with 2×600 milliliters of xylene to remove excess acetone oxime. The aqueous layer was acidified to about pH 1 with 10M HCl and quickly extracted with 4×600 milliliters of xylene. Rotary evaporation under vacuum of a small portion of the combined xylene layers determined the yield of acetone oxime-O-acetic acid to be about 55%. Ion chromatographic analysis did not detect any chloroacetic acid (detection limit less than 30 ppm).

EXAMPLE 3

To a 500 milliliter 3-neck round bottom flask with a nitrogen inlet tube, thermometer, and an outlet tube connected to a receiver and a vacuum pump were added 13.1 grams (0.1 moles) of acetone oxime-O-acetic acid which was prepared in accordance with the procedure of Example 1 and purified by vacuum distillation, 120 milliliters of distilled water, and 60 milliliters (0.6 moles) of 10M hydrochloric acid. With nitrogen bubbling into the solution, the mixture was distilled under a reduced pressure of approximately 100 mmHg at a pot temperature of about 55° C. until a final weight of about 26 grams was obtained. The residual solution was treated with 56 milliliters of isopropyl alcohol and stored overnight in a freezer. The crystals of aminooxyacetic acid hemihydrochloride that separated were collected by filtration, washed with cold isopropyl alcohol, and vacuum-oven dried to produce 7.8 grams (72% yield). Ion chromatographic analysis detected the presence of about 150 ppm of chloroacetic acid.

EXAMPLE 4

Approximately 19 grams (0.145 moles) of acetone oxime-O-acetic acid which was prepared in accordance with the procedure of Example 2 was readily extracted into water from the original xylene solution and was mixed with 58 milliliters (0.58 moles) of 10M HCl. The mixture was distilled under a reduced pressure of approximately 100 mmHg at a pot temperature of 55° C. and while under a nitrogen sparge until a final weight of about 40 grams was obtained. The residual solution was treated with 80 milliliters of isopropyl alcohol. The solution was stored overnight in a freezer and crystals of aminooxyacetic acid hemihydrochloride that separated were collected by filtration, washed with cold isopropyl alcohol, and vacuum-oven dried to produce 10.5 grams. The yield was 66%. Ion chromatographic analysis did not detect any chloroacetic acid (detection limit less than 5 ppm).

Other objects, features and advantages of the present invention will become apparent from the foregoing detailed description and accompanying examples. It should be understood, however, that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A process which comprises:
    (a) reacting an alkali metal or alkaline earth metal hydroxide compound and a solution of an oxime compound to form a first mixture comprising the alkali metal or alkaline earth metal salt of said oxime compound and water;
    (b) adding an organohalide compound while stirring to said first mixture to form a second mixture comprising an O-substituted oxime compound, the alkali metal or alkaline earth metal salt of said oxime compound, water, unreacted organohalide compound and excess oxime compound; and
    (c) heating said second mixture in the presence of an amount of water sufficient to react hydroxide with said unreacted organohalide to obtain an O-substituted oxime compound free of unreacted organohalide compound; wherein said process is conducted at a temperature between about 5° C. and about 60° C.

2. The process according to claim 1, wherein said oxime compound is a compound of the formula $R_1R_2C=NOH$ in which $R_1$ and $R_2$ are the same or different and are hydrogen, or substituted or unsubstituted arylthio, arylsulfonyl, arylsulfinyl, alkylsulfinyl, alkylsulfonyl, alkyl, alkynyl, cycloalkyl, alkenyl, alkoxy, alkoxyalkyl, alkylthio, aryl or aralkyl, or $R_1$ and $R_2$ together may form a substituted or unsubstituted alkylene or alkenylene chain completing a cycloalkyl or cycloalkenyl containing from 3 to about 7 carbon atoms within the ring structure, when substituted containing one or more of the following substituents: alkyl, alkoxy, alkylthio, amido, carboxy, fluoro, nitro, cyano, alkoxycarbonyl, perfluoroalkyl, arylthio, phenoxy, alkylsulfinyl, alkylsulfonyl, arylsulfinyl, alkylaminocarbonyl, dialkylaminocarbonyl, alkylthiocarbonyl, or arylsulfonyl.

3. The process according to claim 1, wherein said reaction mixture formed in step (a) further comprises a non-reactive organic solvent.

4. The process in accordance with claim 1, wherein said process is conducted under ambient atmosphere.

5. The process in accordance with claim 1, wherein said process is conducted at a temperature between about 20° C. and about 55° C.

6. The process according to claim 1, wherein said organohalide compound is a halogenated carboxylic acid of the formula:

XCH(R)COOH wherein R is hydrogen, phenyl, or $C_1$-$C_{14}$ alkyl which is unsubstituted or substituted by phenyl, hydroxy, carboxy, benzyloxy or benzyloxycarbonyl, halogen or amino, and wherein X is halogen.

7. The process according to claim 1, wherein said organohalide compound is a haloacetic acid.

8. The process in accordance with claim 1, further comprising hydrolyzing said O-substituted oxime compound to form the corresponding O-substituted hydroxylamine.

9. The process according to claim 8, wherein said O-substituted hydroxylamine is a compound of the formula:

$H_2N$—O—CH(R)COOH wherein R is hydrogen, phenyl, or $C_1$-$C_{14}$ alkyl which is unsubstituted or substituted by phenyl, hydroxy, carboxy, benzyloxy or benzyloxycarbonyl, halogen or amino.

10. The process according to claim 8, wherein said O-substituted hydroxylamine is aminooxyacetic acid.

11. The process according to claim 1, wherein said process is performed in the absence of azeotropic distillation.

12. A process for the preparation of aminooxyacetic acid which comprises:
(a) reacting an alkali metal or alkaline earth metal hydroxide compound and a solution of an oxime compound to form a first mixture comprising the alkali metal or alkaline earth metal salt of said oxime compound and water;
(b) adding a haloacetic acid while stirring to said first mixture to form a second mixture comprising oxime-O-acetic acid, the alkali metal or alkaline earth metal salt of said oxime compound, water, unreacted haloacetic acid and excess oxime compound;
(c) heating said second mixture in the presence of an amount of water sufficient to react hydroxide with said unreacted haloacetic acid to obtain oxime-O-acetic acid free of unreacted haloacetic acid; and
(d) hydrolyzing said oxime-O-acetic acid to aminooxyacetic acid.

13. A process consisting of:
(a) reacting an alkali metal or alkaline earth metal hydroxide compound and a solution of an oxime compound in an excess of said oxime compound to form a first mixture comprising the alkali metal or alkaline earth metal salt of said oxime compound and water;
(b) adding a haloacetic acid while stirring to said first mixture to form a second mixture comprising an oxime-O-acetic acid, the alkali metal or alkaline earth metal salt of said oxime compound, water, unreacted haloacetic acid and excess oxime compound;
(c) heating said second mixture in the presence of an amount of water sufficient to react hydroxide with said unreacted haloacetic acid to obtain an oxime-O-acetic acid free of unreacted haloacetic acid; and
(d) hydrolyzing said oxime-O-acetic acid to form aminooxyacetic acid.

14. A process which comprises:
(a) reacting an alkali metal or alkaline earth metal hydroxide compound and a solution of an oxime compound in an excess of said oxime compound to form a first mixture comprising the alkali metal or alkaline earth metal salt of said oxime compound and water;
(b) adding a haloacetic acid while stirring to said first mixture to form a second mixture comprising an oxime-O-acetic acid, the alkali metal or alkaline earth metal salt of said oxime compound, water, unreacted haloacetic acid and excess oxime compound, and not subjecting said first mixture to azeotropic distillation, to remove all or a portion of the water from said first mixture; and
(c) heating said second mixture in the presence of an amount of water sufficient to react hydroxide with said unreacted haloacetic acid to obtain an oxime-O-acetic acid free of unreacted haloacetic acid.

* * * * *